United States Patent
Keaveney et al.

(10) Patent No.: US 10,143,823 B2
(45) Date of Patent: Dec. 4, 2018

(54) INTERVENTIONAL MEDICAL SYSTEMS AND IMPROVED ASSEMBLIES THEREOF AND ASSOCIATED METHODS OF USE

(71) Applicant: Medtronic, Inc., Minneapolis, MN (US)

(72) Inventors: James M Keaveney, Galway (IE); Jeffrey Madden, Galway (IE); John Gallagher, Galway (IE)

(73) Assignee: Medtronic, Inc., Minneapolis, MN (US)

( * ) Notice: Subject to any disclaimer, the term of this patent is extended or adjusted under 35 U.S.C. 154(b) by 90 days.

(21) Appl. No.: 15/142,009

(22) Filed: Apr. 29, 2016

(65) Prior Publication Data

US 2017/0312479 A1    Nov. 2, 2017

(51) Int. Cl.
*A61M 25/00* (2006.01)
*A61M 25/01* (2006.01)
(Continued)

(52) U.S. Cl.
CPC .... *A61M 25/0082* (2013.01); *A61M 25/0074* (2013.01); *A61M 25/0147* (2013.01);
(Continued)

(58) Field of Classification Search
CPC .... A61N 1/372; A61N 1/37205; A61N 1/362; A61N 1/3621; A61N 1/3622;
(Continued)

(56) References Cited

U.S. PATENT DOCUMENTS 3,814,104 A    6/1974 Irnich et al.
3,835,864 A    9/1974 Rasor et al.
(Continued)

FOREIGN PATENT DOCUMENTS

EP    1365702    8/2008
EP    1670360    9/2010
(Continued)

OTHER PUBLICATIONS

Marshall et al., "Substernal Lead/Electrode Concepts ", U.S. Appl. No. 62/089,417, filed Dec. 9, 2014, 28 pages.
(Continued)

*Primary Examiner* — Jonathan Miles

(57) ABSTRACT

A system includes a delivery catheter and a separately-packaged implantable medical device assembly. The assembly includes a relatively compact implantable medical device, a support shaft, a tether, and a snare mandrel. The tether, which extends in the support shaft, has a distal portion coupled to the device, at a distal end of the support shaft, and a proximal portion protruding from a proximal end of the support shaft, for engagement by a hook of the snare mandrel. An operator may use the engaged snare mandrel to pull the support shaft into a lumen of an inner shaft of the catheter so that the coupled device comes into engagement with a flared end of the catheter inner shaft. Then, after locking the proximal portion of the tether within the catheter, the operator may advance a receptacle of the catheter over the device.

5 Claims, 7 Drawing Sheets

(51) Int. Cl.
*A61N 1/362* (2006.01)
*A61N 1/372* (2006.01)

(52) U.S. Cl.
CPC ............. *A61N 1/362* (2013.01); *A61N 1/372* (2013.01); *A61N 1/37205* (2013.01); *A61M 2025/0004* (2013.01); *A61M 2025/0096* (2013.01)

(58) Field of Classification Search
CPC ............ A61N 1/3624; A61M 25/0082; A61M 2025/0096; A61F 2002/011; A61F 2/2427; A61F 2/243; A61F 2/2433; A61F 2/2436; A61F 2/2439; A61F 2/95; A61F 2/954; A61F 2/962; A61F 2/966; A61F 2002/9665; A61F 2/97
See application file for complete search history.

(56) References Cited

U.S. PATENT DOCUMENTS

| | | | |
|---|---|---|---|
| 4,103,690 | A | 8/1978 | Harris |
| 5,184,625 | A | 2/1993 | Cottone, Jr. et al. |
| 5,492,119 | A | 2/1996 | Abrams |
| 5,624,736 | A | 7/1997 | Avitall |
| 5,642,736 | A | 7/1997 | Avitall |
| 5,836,960 | A | 11/1998 | Kolesa et al. |
| 5,916,214 | A | 6/1999 | Cosio et al. |
| 6,152,144 | A | 11/2000 | Lesh et al. |
| 6,582,443 | B2 | 6/2003 | Cabek et al. |
| 6,716,238 | B2 | 4/2004 | Elliott |
| 6,783,510 | B1 | 8/2004 | Gibson et al. |
| 6,941,169 | B2 | 9/2005 | Pappu |
| 7,149,587 | B2 | 12/2006 | Wardle et al. |
| 7,497,844 | B2 | 3/2009 | Spear et al. |
| 7,509,169 | B2 | 3/2009 | Eigler et al. |
| 7,566,336 | B2 | 7/2009 | Corcoran et al. |
| 7,623,899 | B2 | 11/2009 | Worley et al. |
| 7,647,124 | B2 | 1/2010 | Williams |
| 8,032,220 | B2 | 10/2011 | Kuzma |
| 8,364,280 | B2 | 1/2013 | Marnfeldt et al. |
| 8,473,023 | B2 | 6/2013 | Worley et al. |
| 8,500,733 | B2 | 8/2013 | Watson |
| 8,504,156 | B2 | 8/2013 | Bonner et al. |
| 8,548,605 | B2 | 10/2013 | Ollivier |
| 8,615,310 | B2 | 12/2013 | Khairkhahan et al. |
| 8,634,919 | B1 | 1/2014 | Hou et al. |
| 8,721,587 | B2 | 5/2014 | Berthiaume et al. |
| 8,781,605 | B2 | 7/2014 | Bornzin et al. |
| 8,795,328 | B2 | 8/2014 | Miles et al. |
| 8,903,513 | B2 | 12/2014 | Ollivier |
| 8,945,145 | B2 | 2/2015 | Tran et al. |
| 8,958,892 | B2 | 2/2015 | Khairkhahan et al. |
| 9,126,032 | B2 * | 9/2015 | Khairkhahan ......... A61N 1/362 |
| 9,155,882 | B2 | 10/2015 | Grubac et al. |
| 9,205,225 | B2 | 12/2015 | Khairkhahan et al. |
| 9,216,293 | B2 | 12/2015 | Berthiaume et al. |
| 9,220,906 | B2 * | 12/2015 | Griswold ........... A61N 1/37205 |
| 9,238,145 | B2 | 1/2016 | Wenzel et al. |
| 9,446,248 | B2 * | 9/2016 | Sheldon ................ A61N 1/371 |
| 9,468,773 | B1 * | 10/2016 | Anderson .............. A61N 1/375 |
| 9,492,674 | B2 * | 11/2016 | Schmidt ............ A61N 1/37205 |
| 2002/0165537 | A1 | 11/2002 | Kelley et al. |
| 2002/0183824 | A1 | 12/2002 | Borgersen et al. |
| 2004/0133098 | A1 | 7/2004 | Kilcoyne et al. |
| 2004/0147973 | A1 | 7/2004 | Hauser |
| 2004/0215307 | A1 | 10/2004 | Michels et al. |
| 2005/0004602 | A1 | 1/2005 | Hart et al. |
| 2005/0004641 | A1 | 1/2005 | Pappu |
| 2005/0136385 | A1 | 6/2005 | Mann et al. |
| 2006/0247753 | A1 | 11/2006 | Wenger et al. |
| 2007/0083230 | A1 | 4/2007 | Javois |
| 2007/0156114 | A1 | 7/2007 | Worley et al. |
| 2008/0057100 | A1 | 3/2008 | Williams et al. |
| 2008/0319424 | A1 | 12/2008 | Muni et al. |
| 2009/0171159 | A1 | 7/2009 | Jorgensen et al. |
| 2009/0287187 | A1 | 11/2009 | Legaspi et al. |
| 2010/0094314 | A1 | 4/2010 | Hernlund et al. |
| 2010/0274227 | A1 | 10/2010 | Khairkhahan et al. |
| 2011/0144572 | A1 | 6/2011 | Kassab et al. |
| 2011/0251660 | A1 | 10/2011 | Griswold |
| 2012/0059448 | A1 | 3/2012 | Parker et al. |
| 2012/0172690 | A1 | 7/2012 | Anderson et al. |
| 2012/0172892 | A1 | 7/2012 | Grubac et al. |
| 2012/0190927 | A1 | 7/2012 | Uihlein |
| 2012/0197373 | A1 | 8/2012 | Khairkhahan et al. |
| 2013/0079798 | A1 | 3/2013 | Tran et al. |
| 2013/0103047 | A1 | 4/2013 | Steingisser et al. |
| 2013/0131591 | A1 | 5/2013 | Berthiaume et al. |
| 2013/0131693 | A1 | 5/2013 | Berthiaume et al. |
| 2013/0253342 | A1 | 9/2013 | Griswold et al. |
| 2013/0253347 | A1 | 9/2013 | Griswold et al. |
| 2014/0018818 | A1 | 1/2014 | Somogyi et al. |
| 2014/0088656 | A1 | 3/2014 | Cabelka et al. |
| 2014/0172034 | A1 | 6/2014 | Bornzin et al. |
| 2014/0180306 | A1 | 6/2014 | Grubac et al. |
| 2014/0249543 | A1 | 9/2014 | Berthiaume et al. |
| 2014/0330219 | A1 | 11/2014 | Quint |
| 2014/0330325 | A1 | 11/2014 | Thompson-Nauman et al. |
| 2014/0330326 | A1 | 11/2014 | Thompson-Nauman et al. |
| 2014/0330329 | A1 | 11/2014 | Thompson-Nauman et al. |
| 2015/0039070 | A1 | 2/2015 | Kuhn et al. |
| 2015/0051612 | A1 * | 2/2015 | Schmidt ............. A61N 1/37205 606/129 |
| 2015/0051613 | A1 | 2/2015 | Schmidt et al. |
| 2015/0051615 | A1 | 2/2015 | Schmidt et al. |
| 2015/0094668 | A1 | 4/2015 | Wood et al. |
| 2015/0094735 | A1 * | 4/2015 | Ward .................... A61N 1/362 606/129 |
| 2015/0095539 | A1 | 4/2015 | Srivastava et al. |
| 2015/0273207 | A1 * | 10/2015 | Tran ...................... A61N 1/059 607/126 |
| 2015/0273212 | A1 | 10/2015 | Berthiaume et al. |
| 2015/0306375 | A1 | 10/2015 | Marshall et al. |
| 2015/0306410 | A1 | 10/2015 | Marshall et al. |
| 2016/0015968 | A1 | 1/2016 | Bonner et al. |
| 2016/0059003 | A1 | 3/2016 | Eggen et al. |
| 2016/0067446 | A1 * | 3/2016 | Klenk .................... A61N 1/05 606/129 |
| 2016/0067447 | A1 * | 3/2016 | Paspa .................... A61N 1/05 606/129 |
| 2016/0220829 | A1 * | 8/2016 | Wood ................. A61N 1/37205 |

FOREIGN PATENT DOCUMENTS

| | | |
|---|---|---|
| WO | 2004028348 A2 | 4/2004 |
| WO | 20130043671 A1 | 3/2013 |
| WO | 20130062793 A1 | 5/2013 |
| WO | 2015017157 A1 | 2/2015 |

OTHER PUBLICATIONS (PCT/US2015/040870) PCT Notification of Transmittal of the International Search Report and the Written Opinion of the International Searching Authority, dated Oct. 14, 2015, 10 pages.
(PCT/US2015/043957) PCT Notification of Transmittal of the International Search Report and the Written Opinion of the International Searching Authority, dated Nov. 11, 2015, 9 pages.
(PCT/US2014/057727) PCT Notification of Transmittal of the International Search Report and the Written Opinion of the International Searching Authority, dated Dec. 8, 2014, 12 pages.
(PCT/US2014/057596) PCT Notification of Transmittal of the International Search Report and the Written Opinion of the International Searching Authority, dated Dec. 5, 2014, 12 pages.
U.S. Appl. No. 14/926,827, filed Oct. 27, 2015.
U.S. Appl. No. 14/598,346, filed Jan. 16, 2015.
U.S. Appl. No. 14/694,083, filed Apr. 23, 2015.
U.S. Appl. No. 14/696,009, filed Apr. 24, 2015.
U.S. Appl. No. 14/620,904, filed Feb. 12, 2015.
U.S. Appl. No. 14/548,958, filed Nov. 20, 2014.
U.S. Appl. No. 14/694,579, filed Apr. 23, 2015.

(56) References Cited

OTHER PUBLICATIONS

U.S. Appl. No. 62/281,312, filed Jan. 21, 2016.
(PCT/US2017/029865) PCT Notification of Transmittal of the International Search Report and the Written Opinion of the International Searching Authority, dated Jul. 28, 2017, 11 pages.

* cited by examiner

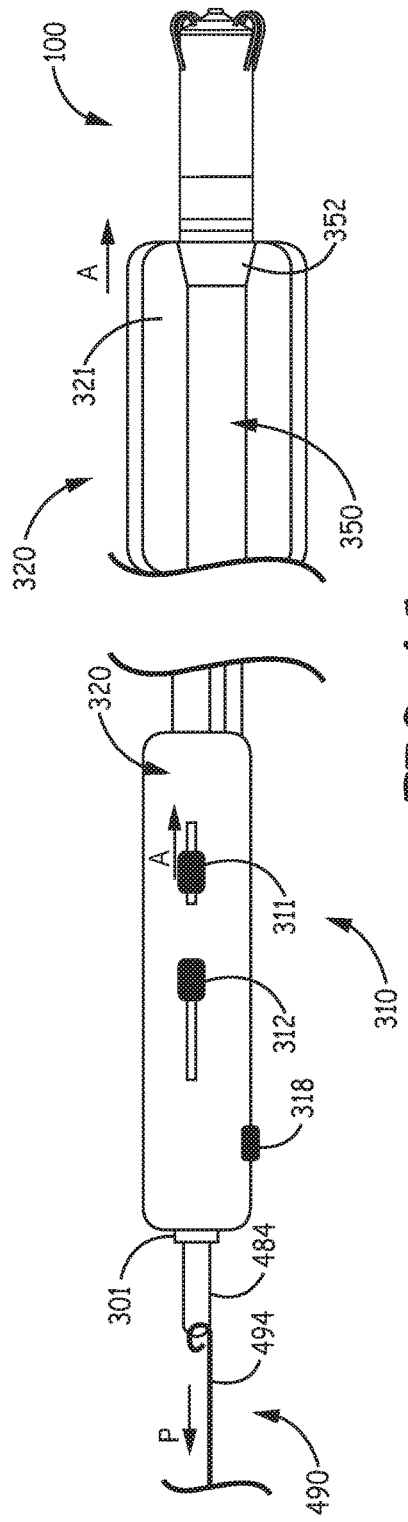
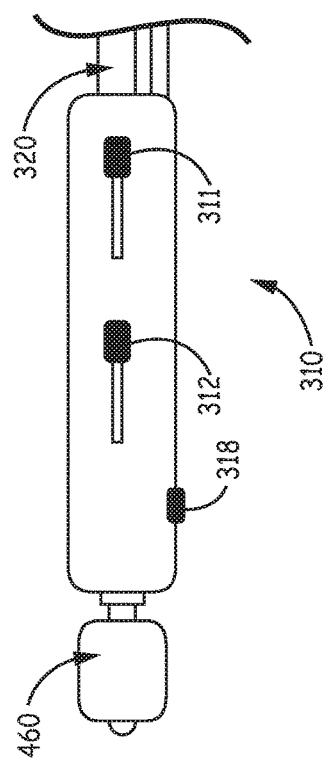
FIG. 4C
FIG. 4D

INTERVENTIONAL MEDICAL SYSTEMS AND IMPROVED ASSEMBLIES THEREOF AND ASSOCIATED METHODS OF USE

TECHNICAL FIELD

The present invention pertains to the delivery of implantable medical devices, and more particularly to systems, improved assemblies thereof and associated methods that facilitate the securing of relatively compact implantable cardiac medical devices to delivery catheters.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues sometimes associated with elongate lead wires are well known to those skilled in the art and have motivated the development of cardiac pacing devices that are wholly contained within a relatively compact package for implant in close proximity to the pacing site, for example, within a right ventricle RV of the heart.

FIG. 1 is a schematic showing an example of an implanted relatively compact implantable medical device 100. FIG. 1 illustrates medical device 100 having been delivered through a catheter 200, which an operator has maneuvered up through the inferior vena cava IVC and the right atrium RA into the right ventricle RV. Device 100 is shown deployed at an implant site in the right ventricular apex. Another potential cardiac implant site may be within an appendage of a right atrium RA, or within a coronary vein. Device 100 and catheter 200 may be similar to the device and tool, respectively, described in the commonly assigned United States Patent Application US 2015/0094668.

FIG. 1 further illustrates device 100 including a hermetically sealed enclosure 105 containing pulse generator electronics and a power source (not shown), pace/sense electrodes 111, 112 formed on an exterior surface of enclosure 105, and a fixation member, for example, formed from a plurality of elastically deformable fingers 115 mounted to a distal end of enclosure 105, in proximity to electrode 111, in order to fix, or secure electrode 111 against the endocardial surface at the implant site. Enclosure 105 is preferably formed from a biocompatible and biostable metal such as titanium overlaid with an insulative layer, for example, medical grade polyurethane or silicone, except where electrode 112 is formed as an exposed portion of the metal. An hermetic feedthrough assembly, such as any suitable type known to those skilled in the art, couples electrode 111 to the pulse generator contained within device enclosure 105.

Device 100 is shown fixed at the implant site by fingers 115 of the fixation member thereof, but still secured to catheter 200 by a flexible tether 280, which extends out from a distal opening 203 of catheter 200, being joined to an engaging member 121 of device 100. Thus, the operator, via tether 280, is able to test the fixation of device 100 at the implant site, and/or remove device 100 from the implant site for repositioning at a more suitable site, if necessary. Once satisfied with the implant of device 100, the operator can separate tether 280 from device 100, for example, by releasing an end of one length 281 of tether 280, and then pulling on an end of another length 282 of tether 280 to withdraw an entirety of length 282 proximally through delivery catheter 200 so that tether length 281 is pulled distally and through engaging member 121.

Securing device 100 to catheter 200 with tether 280 is typically accomplished by a process in which tether 280 is looped through engaging member 121, after which first and second lengths 281, 282 of tether 280 are threaded through one or more lumens of catheter 200 such that opposing ends thereof protrude out from a proximal opening 201 of catheter 200. Because this process may be somewhat tedious, a manufacturer of device 100 and catheter 200 may secure the two together as a system, and provide the system to the operator in a single sterile package. However, due to shelf life considerations, the packaging of such a device separately from the associated catheter may be preferred, so that alternative means for securing the device to the catheter may be desired, to increase the ease by which an operator may secure the device to the catheter at the time of an implant procedure.

SUMMARY

Interventional medical systems disclosed herein include a delivery catheter and a separately-packaged implantable device assembly. According to some embodiments, the delivery catheter includes an elongate inner shaft having a flared end that surrounds a distal-most opening of a lumen of the inner shaft, and a receptacle in sliding engagement with the inner shaft; and the device assembly includes a relatively compact implantable medical device, a support shaft, and a tether that extends within the support shaft with a distal portion thereof, which protrudes from a distal end of the support shaft, coupling the device to the support shaft. The device assembly may further include an elongate snare mandrel that has a distal end formed in a hook to engage with a proximal portion of the tether, which protrudes from a proximal end of the support shaft, so that an operator may use the snare mandrel to pull the support shaft into the lumen of the inner shaft of the delivery catheter and bring the coupled device into engagement with the flared end of the inner shaft. When the coupled device is thus engaged, the operator may lock the proximal portion of the tether within the delivery catheter and then advance the receptacle of the catheter over the device so that the device is contained therein. In some embodiments, the implantable device assembly further includes a tether retainer attachable and detachable from the proximal portion of the tether.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIGS. 4A-D are various plan views of the system of FIG. 2A outlining some methods for securing a relatively compact implantable medical device of the system to a delivery catheter of the system.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figures 2A, 2B:
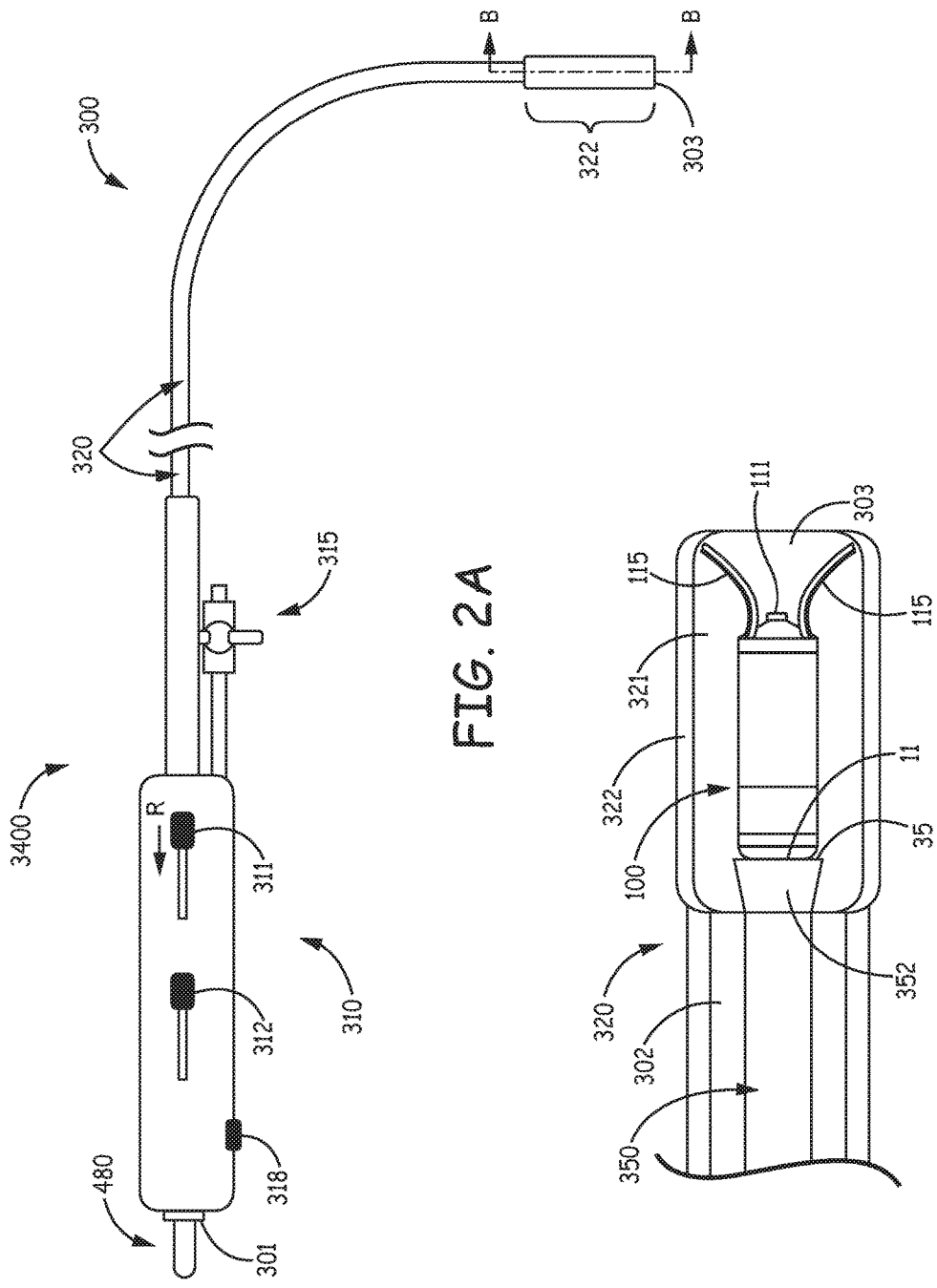
FIG. 2A is a plan view of an interventional medical system, according to some embodiments.
FIG. 2B is a partial cross-section view through section line B-B of FIG. 2A, according to some embodiments.

FIG. 2A is a plan view of an interventional medical system 3400, according to some embodiments. FIG. 2A illustrates a delivery catheter 300 of system 3400 including a handle 310, an elongate outer shaft 320, and a flushing assembly 315 coupled to handle 310. FIG. 2B, which is a partial cross-section view through section line B-B of FIG. 2A, shows a distal-most portion 322 of outer shaft 320 defining a receptacle 321 that has a distal-most opening 303, wherein receptacle 321 is sized to contain an implantable medical device of system 3400, such as device 100, for delivery to an implant site. FIG. 2B illustrates an inner shaft 350 of catheter 300 extending within a lumen 302 of outer shaft 320 that is in fluid communication with receptacle 321. According to the illustrated embodiment, receptacle 321 is in sliding engagement with inner shaft 350, and may be retracted and advanced relative to inner shaft 350 (for the purposes described in greater detail below) by means of a first control member 311 of handle 310 (FIG. 2A), to which outer shaft 320 is coupled. Furthermore, lumen 302 of shaft 320 may be flushed via flushing assembly 315.

Figure 1:
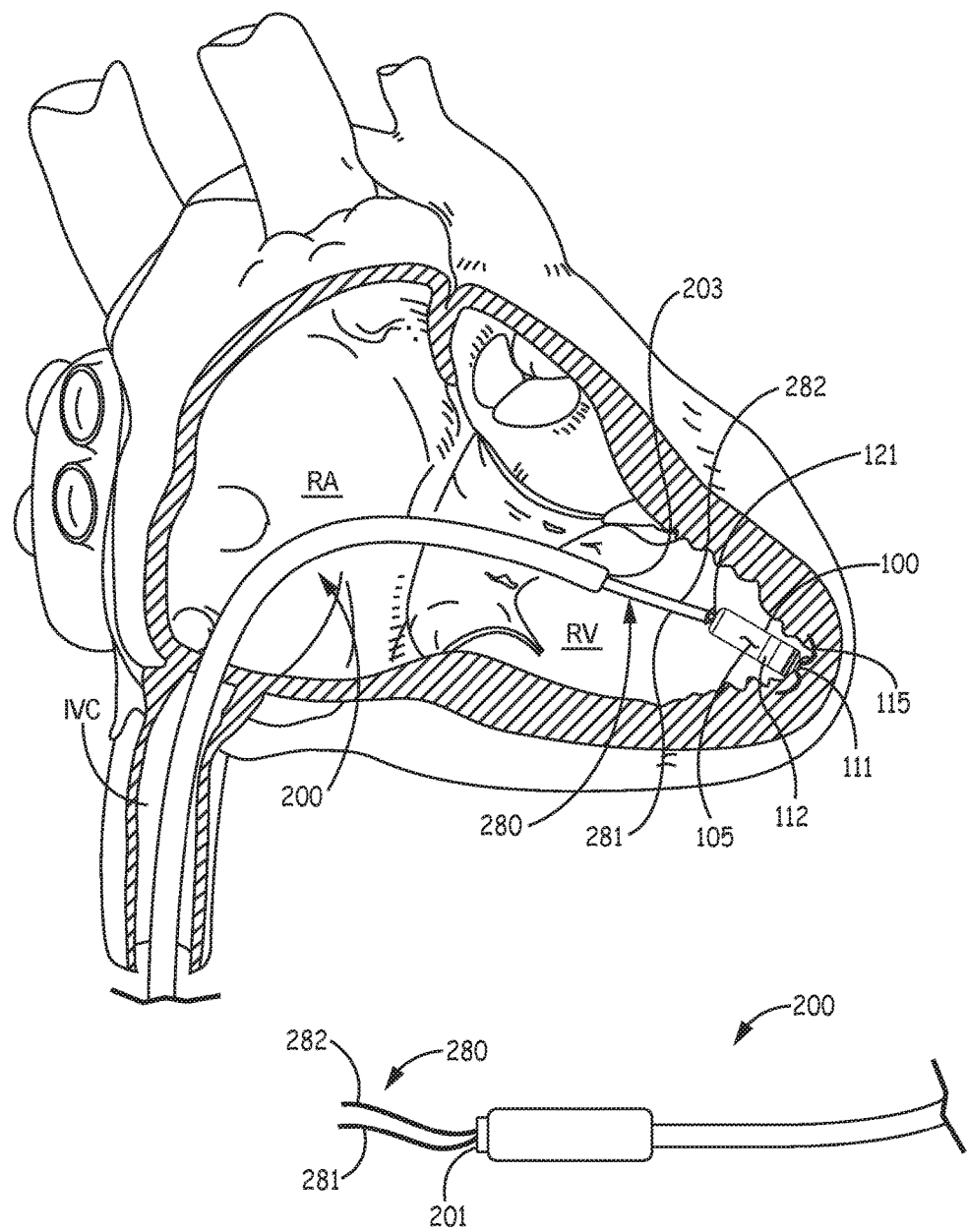
FIG. 1 is a schematic showing an example of an implanted relatively compact implantable medical device.

According to some embodiments, outer shaft 320 may be constructed in a similar fashion to a deployment tube of a tool described in co-pending and commonly assigned U.S. Patent Application 2015/0094668, Ser. No. 14/039,937. For example, outer shaft 320 may be formed by a stainless steel braid-reinforced medical grade polymer, for example, one or more appropriate grades of polyether block amide, which are arranged for decreasing stiffness from handle 310 to distal-most portion 322 (e.g., including PEBAX® 3533, 6333, 4033, and 7233), and receptacle 321 may have a diameter of up to approximately 0.3 inch (7.6 mm). Distal-most portion 322 may have a radiopaque filler blended therein, or a radiopaque marker (e.g., Tungsten-filled Vestamid®) bonded thereto, either according to methods known to those skilled in the art. FIG. 2A further illustrates handle 310 including a second control member 312 which may be coupled to a pull-wire mounted in inner shaft 350, wherein the pull-wire is operable, via control member 312, to deflect inner and outer shafts 350, 320 for navigation of catheter 300 to an implant site, for example, as described above in conjunction with FIG. 1.

Figure 3A:
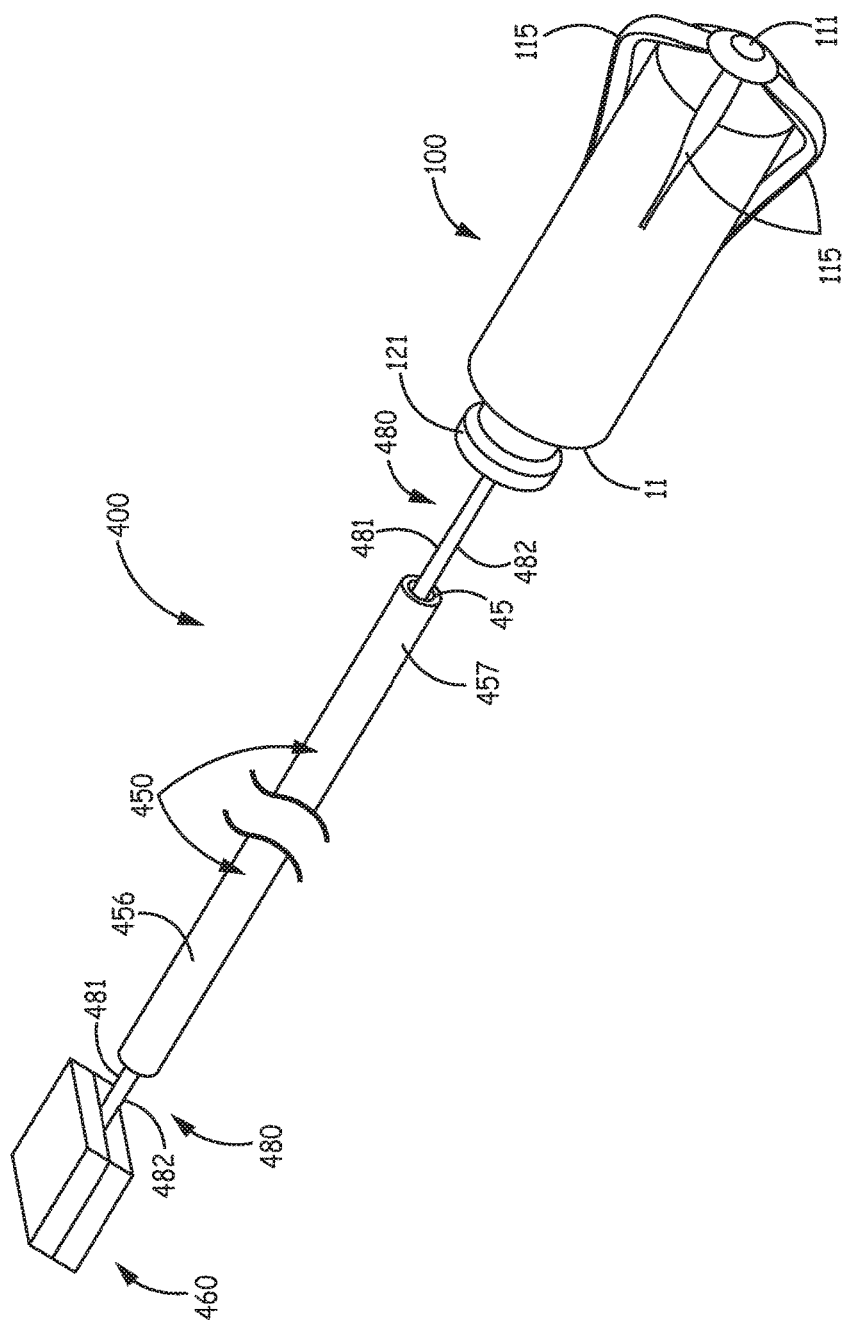
FIG. 3A is a perspective view of a medical device assembly of the system of FIG. 2A, according to some embodiments.
Figure 3B:
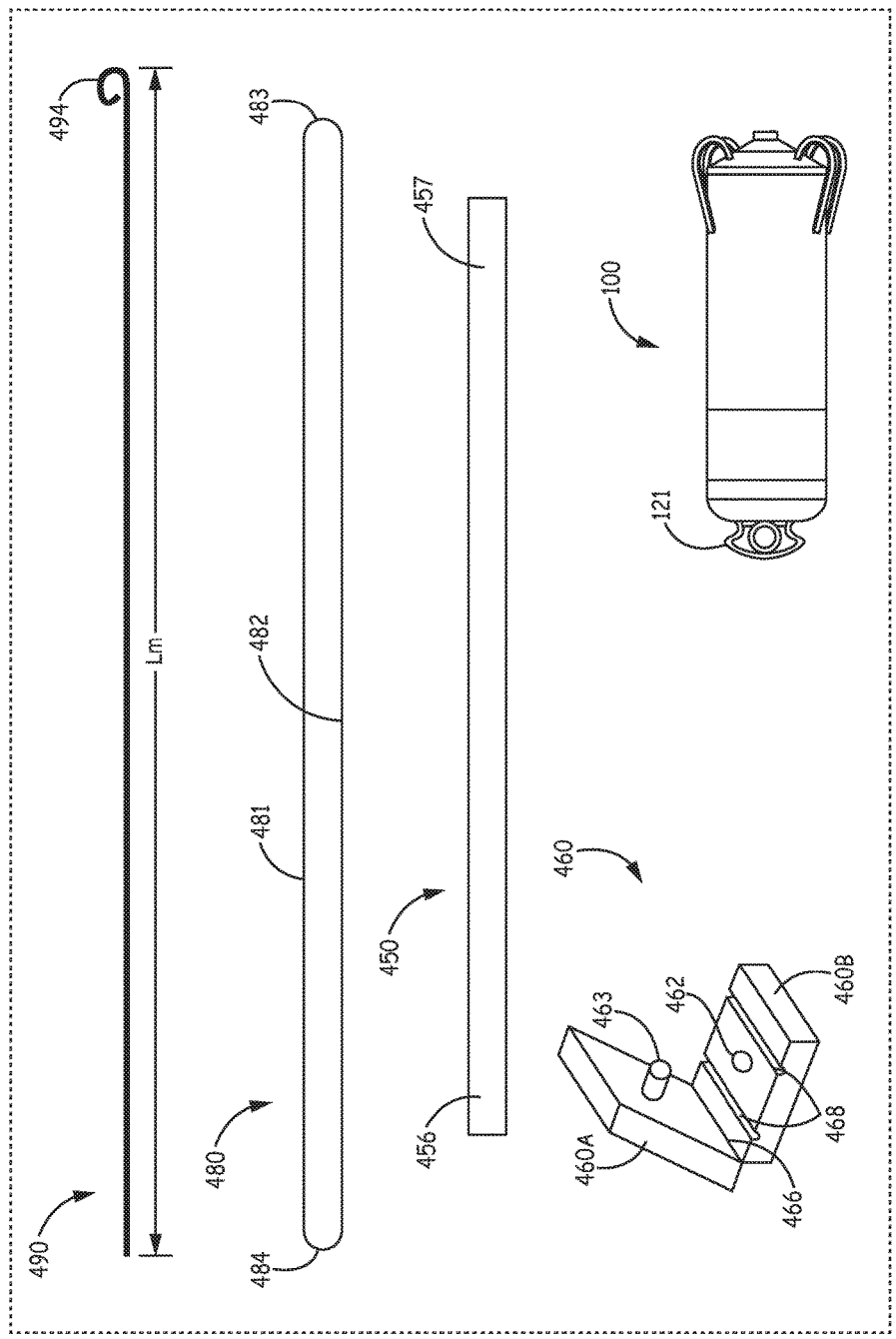
FIG. 3B is a plan view of various parts of the medical device assembly, according to some embodiments.

FIG. 2B further illustrates device 100 being secured to catheter 300 and contained within receptacle 321 of outer shaft 320 such that a proximal end 11 of device 100 is engaged with a flared end 352 of inner shaft 350. According to the illustrated embodiment, flared end 352 defines a distal-most opening 35 into a lumen 305 of inner shaft 350 (seen in FIGS. 4A-B), which lumen 305 is sized to receive a support shaft 450 of a medical device assembly 400 of system 3400, which is shown in FIGS. 3A-B. (Note that inner shaft 350 may include another lumen that extends alongside lumen 305 and that receives the aforementioned pull wire.) According to an exemplary embodiment, flared end 352 may be formed from a polyether block amide, for example, PEBAX® 7233, and the remainder of inner shaft 350 may be formed by a tube, for example, extruded polyether block amide, polyurethane, or silicone rubber, or a composite thereof, which includes an overlay, for example, formed of braid-reinforced polyether block amide.

FIG. 3A is a perspective view of medical device assembly 400, which is configured for securing a relatively compact medical device, such as device 100, to catheter 300, and is packaged separately from catheter 300, according to some embodiments. Thus, as alluded to above, a shelf life of catheter 300 in its own package is independent of that of device 100 when packaged separately as part of assembly 400. This may be particularly significant when electrode 111 of device 100 is manufactured with an anti-inflammatory steroid embedded therein. FIG. 3A illustrates assembly 400 including device 100, support shaft 450, and an elongate tether 480, wherein tether 480 is coupled to device 100, and has a first length 481 extending within a lumen 45 of support shaft 450, and a second length 482 extending alongside first length 481, either within lumen 45, or within another lumen of support shaft 450 (not shown) that extends alongside lumen 45, or adjacent an outer surface of support shaft 450. FIG. 3A further illustrates device assembly including an optional tether retainer 460 attached to a proximal portion 484 of tether 480 (seen in FIG. 3B) in proximity to proximal end 456 of support shaft 450.

FIG. 3B is a plan view of various parts of device assembly 400, according to some embodiments, wherein the parts are shown separated from one another. FIG. 3B illustrates the parts of assembly 400 further including an elongate snare mandrel 490, which has a distal end 494 formed in a hook. According to the illustrated embodiment, the hook of distal end 494 is designed to engage with proximal portion 484 of tether 480, according to a method described below in conjunction with FIGS. 4A-C. FIG. 3B further illustrates proximal and distal portions 484, 483 of tether 480 each joining first and second lengths 481, 482 of tether 480 together at opposite ends thereof; and, when tether 480 is assembled together with support shaft 450, as illustrated in FIG. 3A, tether proximal portion 484 protrudes from proximal end 456 of shaft 450 and tether distal portion 483 protrudes from distal end 457 of shaft 450. Thus, tether proximal portion 484 can be engaged by mandrel 490, for example, as illustrated in FIG. 4A, and tether distal portion 483 can couple to engaging member 121 of device 100, for example, as illustrated in FIG. 4B.

With further reference to FIG. 3B, optional tether retainer 460 is shown in an opened position with first and second parts 460A, 460B thereof separated from one another. FIG. 3B illustrates second part 460B including a pair of grooves 468, to receive first and second lengths 481, 482 therein, and a receptacle 462 to receive a protrusion 463 of first part 460A in interlocking engagement therewith when retainer 460 is in a closed position, for example, as illustrated in FIG. 3A. According to an exemplary embodiment, retainer 460 is formed from any suitable medical grade plastic that has living hinge properties (e.g., Polypropylene Pro-Fax™ 6523) so that first and second parts 460A, 460B may be joined together by such a hinge 466.

FIGS. 4A-D are various plan views of system 3400 outlining some methods for securing device 100 within receptacle 321 of catheter 300.

Figure 4A:
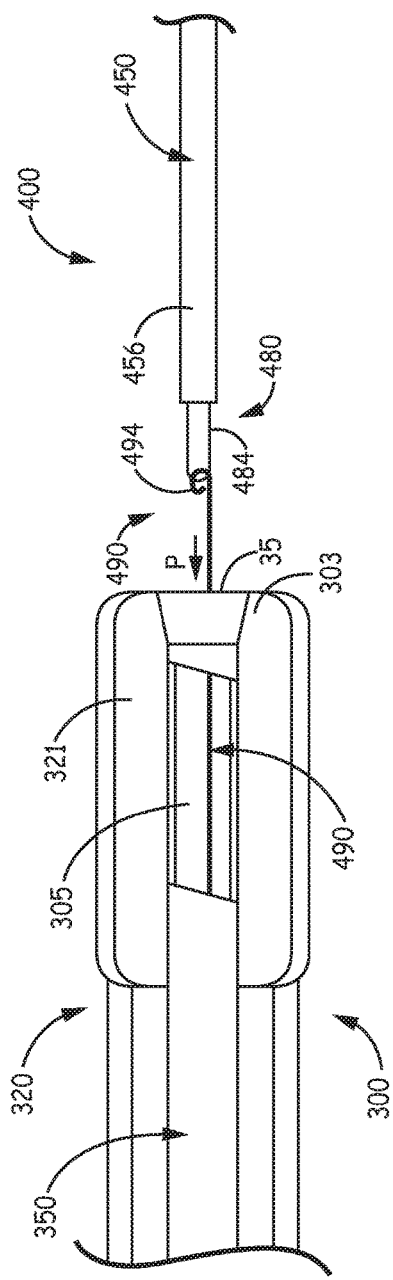
Figure 4B:
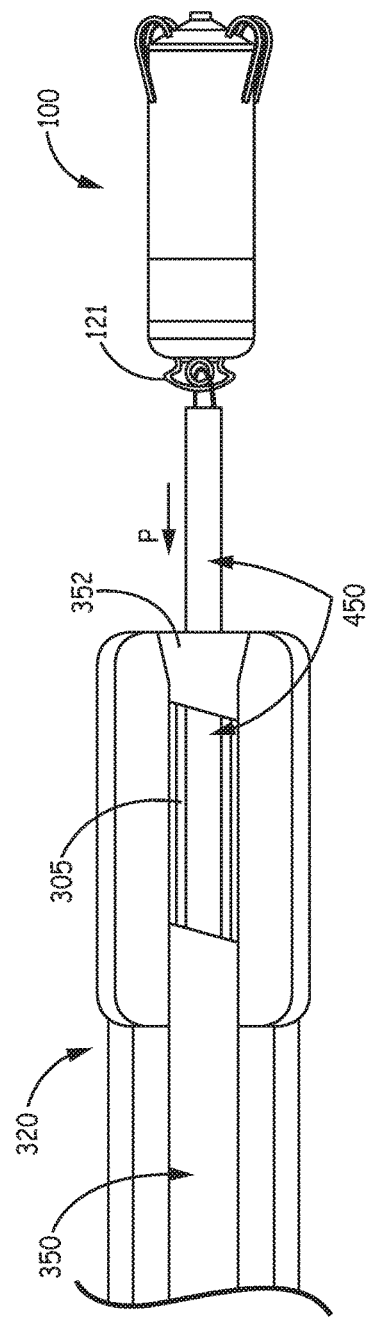

With reference to FIG. 4A, an operator has inserted snare mandrel 490 into lumen 305 of inner shaft 350 of catheter 300, so that the hook formed in distal end 494 of snare mandrel 490 protrudes from distal-most opening 35 of inner shaft 350. FIG. 4A illustrates distal-most opening 35 having been exposed at, or distal to, distal-most opening 303 of receptacle 321 by retracting receptacle 321 relative to inner shaft 350, for example, by moving first control member 311 per arrow R (FIG. 2A). With reference back to FIG. 3B, a length $L_m$ of snare mandrel 490 is sufficiently greater than a length of catheter inner shaft 350, so that a proximal end of mandrel 490 protrudes from a proximal end of catheter 300, for example, from a proximal port opening 301 shown in FIG. 2A. FIG. 4A further illustrates device assembly 400 oriented so that tether proximal portion 484, protruding from support shaft proximal end 456, is directed toward distal-most opening 35 of inner shaft 350 of catheter 300. Thus, the operator can engage the hook at distal end 494 of snare mandrel 490 with tether proximal portion 484, as shown in FIG. 4A, and then apply a pull force to the proximal end of the inserted snare mandrel 490 to pull support shaft 450, per arrow P, into lumen 305 of catheter inner shaft 350, as illustrated in FIG. 4B.

When, in some embodiments, lumen 305 of catheter inner shaft has a diameter of approximately 1.6 mm, a maximum outer diameter of each of snare mandrel 490 and support shaft 450 may be no greater than approximately 1.14 mm, so that each may be received in sliding engagement within lumen 305. According to an exemplary embodiment, snare mandrel 490 is formed from a medical grade stainless steel, tether 480 is formed from a polyester fiber having a fluoropolymer coating such as PTFE, and support shaft 450 is formed from an extruded polyether block amide, polyurethane, or silicone rubber, or a composite thereof.

With reference to FIG. 4C, the operator may continue to pull, per arrow P, until tether proximal portion 484 protrudes from proximal port opening 301 of catheter 300 and the coupled medical device 100 comes into engagement with flared end 352 of catheter inner shaft 350. According to some methods, before advancing receptacle 321 of catheter 300 relative to inner shaft 350, per arrow A, so that device 100 is contained in receptacle 321, as shown in FIG. 2B, the operator may lock tether 480 within catheter 300, for example, via a locking member 318 mounted in handle 310. Locking member 318 is described below in conjunction with FIG. 5. Finally, in those embodiments of device assembly 400 that include tether retainer 460, the operator, having detached retainer 460 from tether proximal portion 484 prior to engaging mandrel 490 therewith, re-attaches retainer 460 to tether proximal portion 484, as illustrated in FIG. 4D, prior to navigating system 3400 to an implant site. Once the operator has navigated distal-most opening 303 into proximity with a target implant site, the operator may retract outer shaft 320 relative to inner shaft 350 and the contained device 100, for example, by moving control member 311 per arrow R (FIG. 2A), in order to engage fixation member fingers 115 of device 100 with tissue at the site. Once fixation member fingers 115 are engaged, in addition to evaluating an electrical performance of device 100 at the site, the operator may test the fixation of device 100 by grasping retainer 460 and applying a pull force to tether 480. If the operator determines that device 100 needs to be repositioned to a more suitable site, the operator, again grasping retainer 460, may apply a pull force sufficient to disengage fingers 115. But, if the operator is satisfied with the implant, the operator may detach retainer 460, unlock tether 480, cut tether proximal portion 484, and pull on one of tether lengths 481, 482 to withdraw an entirety of the length proximally through delivery catheter 200 so that the other length is pulled distally out through device engaging member 121.

Figure 5:
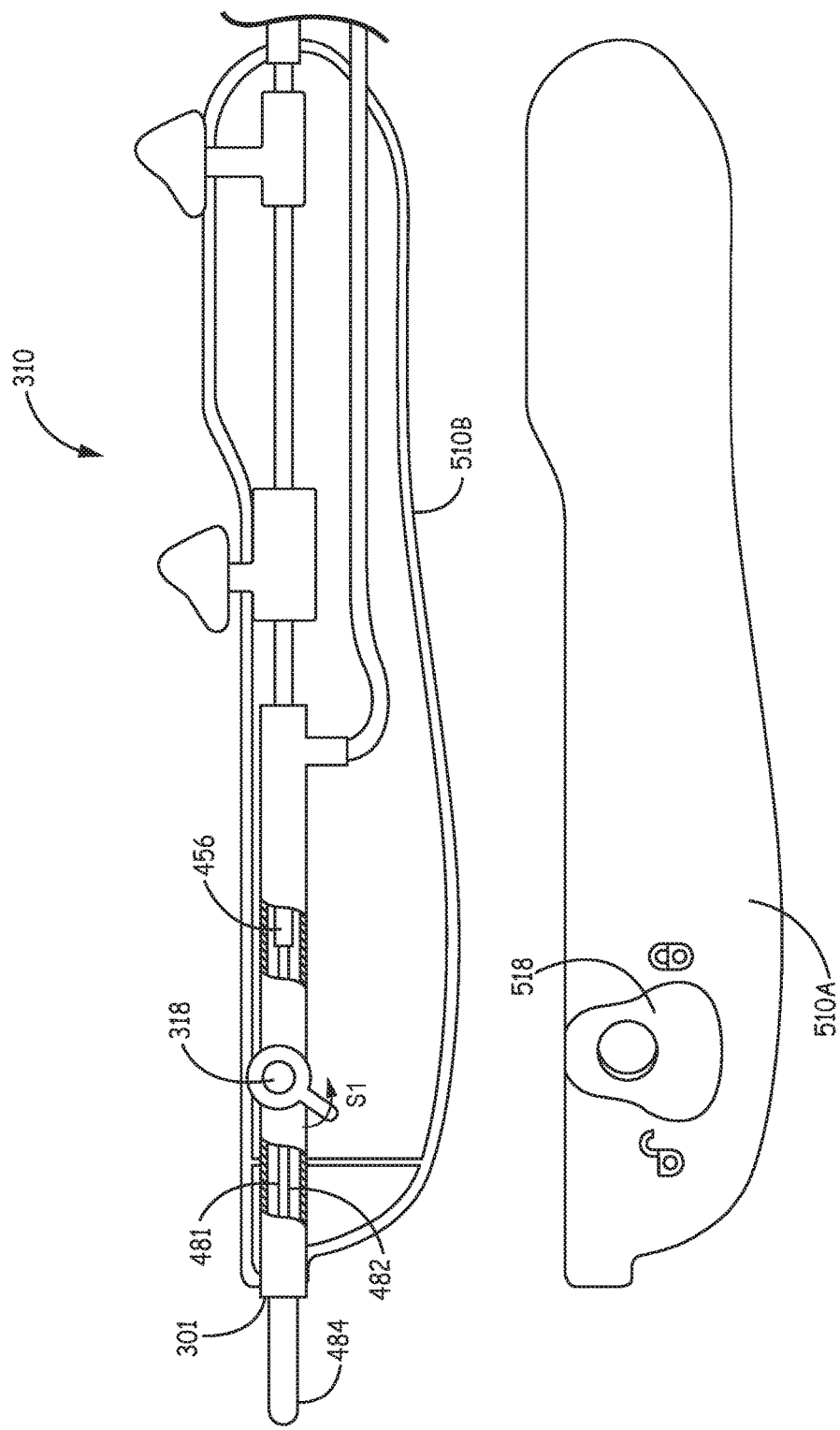
FIG. 5 is a plan view of an internal configuration of a catheter handle, according to some embodiments.

FIG. 5 is a plan view of an internal configuration of catheter handle 310, according to some embodiments, wherein a first portion of an outer surface, or shell 510A of handle 310 is removed, being separated from a second portion of the shell 510B. FIG. 5 illustrates tether lengths 481, 482 extending within locking member 318 and tether proximal portion 484 protruding from proximal port opening 301. Locking member 318 may be a stopcock type valve, known to those skilled in the art, wherein a lever thereof, when rotated per arrow S1, closes valve to clamp around, and secure tether lengths 481, 482 in handle 310. According to the illustrated embodiment, the lever of locking member 318 may extend through a corresponding aperture 518 formed in a recessed surface of handle shell first portion 510A, when handle shell portions 510A, 510B are secured together. FIG. 5 further illustrates proximal end 456 of support shaft 450 extending within handle 310, according to some embodiments.

In the foregoing detailed description, the invention has been described with reference to specific embodiments. However, it may be appreciated that various modifications and changes can be made without departing from the scope of the invention as set forth in the appended claims.

The invention claimed is:

1. A method for securing an implantable medical device within a receptacle of a delivery catheter, the method comprising:

retracting the receptacle of the delivery catheter relative to an inner shaft of the delivery catheter so that a distal-most opening of an elongate lumen of the inner shaft is exposed at, or distal to, a distal-most opening of the receptacle;

inserting an elongate snare mandrel into the lumen of the inner shaft of the delivery catheter so that a hook of the snare mandrel protrudes from the exposed distal-most opening of the inner shaft and a proximal end of the snare mandrel protrudes from a proximal port opening of the delivery catheter;

engaging the hook of the snare mandrel with a proximal portion of a tether that protrudes from a proximal end of a tether support shaft, the tether extending within a lumen of the support shaft, and a distal portion of the tether protruding from a distal end of the support shaft and being coupled to the medical device;

applying a pull force to the proximal end of the inserted snare mandrel, after engaging the hook thereof, to pull the support shaft into the lumen of the delivery catheter inner shaft so that the coupled medical device comes into engagement with a flared end of the delivery catheter inner shaft, the flared end surrounding the distal-most opening of the inner shaft lumen;

locking the proximal portion of the tether within the delivery catheter after applying the pull force; and advancing the receptacle of the delivery catheter, relative to the inner shaft thereof, over the medical device so that the device is contained within the receptacle, after locking the proximal portion of the tether.

2. The method of claim 1, further comprising:
  detaching a tether retainer from the proximal portion of the tether, before engaging the hook of the snare mandrel therewith; and
  re-attaching the tether retainer to the proximal portion of the tether, after applying the pull force.

3. The method of claim 2, wherein detaching the retainer comprises opening opposing first and second parts thereof away from one another to release lengths of the proximal portion of the tether from a press fit between the parts; and re-attaching the retainer comprises closing the opposing first and second parts toward one another so that the lengths of the tether proximal portion are captured in the press fit therebetween, and the opposing first and second parts interlock with one another.

4. An interventional medical system including a delivery catheter and an implantable medical device assembly packaged separately from the delivery catheter, the delivery catheter comprising an elongate inner shaft, and a receptacle in sliding engagement with the inner shaft, the receptacle being sized to contain the medical device therein and having a distal-most opening, and the inner shaft including an elongate lumen extending from a distal opening thereof at a flared distal end of the inner shaft to a proximal opening thereof at a proximal port opening of the catheter; and the assembly comprising:
  a compact implantable medical device including a pulse generator and a hermetic enclosure containing the pulse generator;
  an elongate support shaft extending from a proximal end thereof to a distal end thereof and including a lumen extending along a length of the support shaft, the lumen including a proximal opening at the proximal end of the shaft, and a distal opening at the distal end of the shaft, and an entirety of the support shaft being sized to fit in sliding engagement within the lumen of the inner shaft;
  an elongate tether including a first length, a second length, a distal portion, and a proximal portion, each of the distal and proximal portions joining the first length to the second length at opposite ends thereof, the first length extending within the lumen of the support shaft, the proximal portion protruding from the proximal end of the support shaft, the distal portion protruding from the distal end of the support shaft, and the distal portion being coupled to the implantable medical device; and
  an elongate snare mandrel extending over a length from a proximal end thereof to a distal end thereof, the distal end being formed in a hook configured to engage with the proximal portion of the tether, a length of the snare mandrel being greater than the length of the inner shaft of the catheter, and the snare mandrel being sized to fit in sliding engagement within the lumen of the inner shaft.

5. The system of claim 4, wherein the assembly further comprises a tether retainer configured to be attached to, and detached from, the proximal portion of the tether, the tether retainer including opposing first and second parts configured to interlock with one another and to hold the proximal portion of the tether in a press fit therebetween when interlocked with one another.

* * * * *